(12) United States Patent
Patil

(10) Patent No.: US 8,668,945 B2
(45) Date of Patent: *Mar. 11, 2014

(54) HERBAL MILK REPLACER COMPOSITIONS FOR CALF

(76) Inventor: Prashant Neminath Patil, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/508,241

(22) PCT Filed: Nov. 4, 2010

(86) PCT No.: PCT/IN2010/000725
§ 371 (c)(1),
(2), (4) Date: May 4, 2012

(87) PCT Pub. No.: WO2011/055387
PCT Pub. Date: May 12, 2011

(65) Prior Publication Data
US 2012/0237622 A1    Sep. 20, 2012

(30) Foreign Application Priority Data

Nov. 7, 2009  (IN) .......................... 2329/MUM/2009

(51) Int. Cl.
*A61K 36/00* (2006.01)

(52) U.S. Cl.
USPC ......................................................... 424/775

(58) Field of Classification Search
None
See application file for complete search history.

(56) References Cited

U.S. PATENT DOCUMENTS

| 4,642,317 A | | 2/1987 | Palmquist et al. ............ 514/558 |
| 6,080,401 A | * | 6/2000 | Reddy et al. ................. 424/93.3 |
| 2012/0263697 A1 | | 10/2012 | Patil |
| 2012/0263811 A1 | | 10/2012 | Patil |
| 2012/0288578 A1 | | 11/2012 | Patil |

FOREIGN PATENT DOCUMENTS

| DE | 202006000487 | | 4/2006 | |
| DE | 102006042149 | | 5/2007 | |
| KR | 2003044731 A | * | 6/2003 | |
| KR | 20090097727 | | 9/2009 | |
| WO | WO 00/74696 | * | 12/2000 | ............ A61K 35/78 |
| WO | 0203813 | | 1/2002 | |
| WO | WO 02/26261 | * | 4/2002 | ............ A61K 47/00 |
| WO | 2004052122 | | 6/2004 | |

OTHER PUBLICATIONS

Meeske, R. et al., "The effect of concentrate supplementation on the productivity of grazing Jersey cows on a pasture based system." In: South African Journal of Animal Science, vol. 36/22006. pp. 105,110, 2006.
Castillo, A.R. et al., "Effects of feeding rations with genetically modified whole-cottonseed to lactating Holstein cows." In: Journal of Diary. Science, vol. 87/6, 2004. pp. 1778-1785.
PCT Search Report for PCT/IN09/000571, Jun. 18, 2010.
PCT Search Report for PCT/IN10/000726, Apr. 21, 2011.
PCT Search Report for PCT/IN09/000572, Jun. 14, 2010.
PCT Search Report for PCT/IN10/000725.

* cited by examiner

*Primary Examiner* — Suzanne M Noakes
*Assistant Examiner* — Stephen Chong
(74) *Attorney, Agent, or Firm* — C. Rachal Winger; K&L Gates, LLP

(57) ABSTRACT

The present invention relates generally to herbal milk replacer compositions for feeding animals, particularly young animals, and its method of making and feeding, and more particularly relates to shelf-stable and cheaper herbal milk replacer compositions for body weight gain along with overall development of calves to early complete functional maturity and also prevents any infection by acting as immunobooster. The herbal milk replacer compositions comprises effective amount of an mixture of herbal extract and/or at least one bioactive fraction from medicinal herbs and one or more additives selected from Energy Source, Protein Source, Chelated/organic Mineral Mixture, Vitamins, Salt, Toxin destroyer and Biocide; and process for the preparation of such extracts and herbal milk replacer compositions. The mixture of herbal extract comprising medicinal herbs selected from *Emblica officinalis, Tinospora cordifolia, Embelia basaal, Cyprus rotundus, Asparagus racemosus* and *Lepidium sativam*. The effective amount in the composition is 1 to 10% (w/w) herbal mixture, 30 to 70% (w/w) Energy Source, 20 to 70% (w/w) Protein Source, 2% (w/w) Chelated/organic Mineral Mixture, 1% (w/w) Salt, 0.1% (w/w) Vitamins, 0.1% (w/w) Toxin Destroyer, 0.03% (w/w) Biocide.

20 Claims, No Drawings

HERBAL MILK REPLACER COMPOSITIONS FOR CALF

This application is a US national stage entry of PCT/IN2010/000725 filed Nov. 4, 2010 which claims priority to Indian Application No. 2329/MUM/2009 filed Nov. 7, 2009, each of which are incorporated by reference in their entirety herein.

FIELD OF THE INVENTION

The present invention relates generally to herbal milk replacer compositions for feeding animals, particularly young animals, and its method of making and feeding, and more particularly relates to shelf-stable and cheaper herbal milk replacer compositions for overall development of calves to early complete functional maturity and also for prevention of any infection by acting as immunobooster.

BACKGROUND OF THE INVENTION

It is well known that in the early stages of life for a mammal, mother's milk is the ideal source of nutrition. In the livestock industry, calves that are raised for veal and for herd replacement commonly are weaned from colostrum-rich cow's milk to a nutrient-rich milk replacer within a few days following birth. Animals having monogastric digestion are frequently fed milk or a milk substitute during their early life. Unfortunately for many young mammals, whether by tragedy or by economic necessity, as in the case of animals whose milk is commercially valuable, mother's milk is not always available. In these instances, the use of a milk replacing composition is required. Milk replacers are intended to replace whole milk and thus to provide an economic alternative to whole milk in the raising of the young animal.

Research has been ongoing for many years in an effort to determine how calves respond to various food ingredients and to formulate milk replacers to respond to the nutritive needs of pre-ruminants. A summary of milk replacer research reported in Trevor Tomkins, Sowinski, J. and Drackley, J. K., New Developments in Milk Replacers for Pre-Ruminants, 55th Minnesota Nutrition Conference & Roche Technical Symposium, 1994, pp. 71-82. This paper notes, on page 72, that the nutrient requirements of the calf are not well understood in relation to our understanding of the nutrient requirements of the young of other species. D. C. Church, Digestive Physiology and Nutrition of Ruminants, Church, Dept. of Animal Science, Oregon State Univ., 1972, Vol. 3, p. 122 reports that calf scours (diarrhea) has continued to be a problem with calves, and that although whole milk produces good calves, the protein to energy ratio may be too high for maximum weight. It has also been reported that weight gains of calves to eight weeks of age were increased by adding 3% cream or an equivalent amount of energy from glucose to 3.5% butterfat milk. J. H. B. Roy, The Calf Nutrition and Health, Penn. State Univ. Press, p. 100, reported that in France, a comparison of liquid diets containing 2.3-6.9% glucose and 0.5-3.5% fat showed that the highest weight gains were obtained when the highest concentration of glucose and of fat was used. Although retention of nitrogen was highest at the highest level of glucose, diarrhea was more frequent; this finding led to the recommendation that milk substitutes should contain not more than 2-3% glucose and a fat content of 2.5-3.5%. It has been reported that when more than 500 grams of lactose or glucose are given daily, there is a tendency for the calf to have diarrhea.

There exist many formulations for foodstuffs for neo-natal animals that incorporate dried milk products and vitamin and mineral supplements. The common feature of these prior art compositions is that they derive most of their protein content from a milk source ingredient such as skim milk, buttermilk, whole whey, delactosed whey, casein, milk albumin, and/or whey protein concentrate. Milk source ingredients are used extensively in traditional milk replacers because the existing health data relating to young mammals fed milk replacer diets based on non-milk source ingredients is poor. That is, animals fed with prior art milk replacers having protein sources other than milk proteins are known to suffer from protein deficiencies that can potentially result in debilitating illnesses. This data suggests that only milk-based milk replacers can be used to obtain a healthy young animal.

In the case of dairy calves, the susceptibility to disease is an acute and persistent problem and manifests itself most frequently in the form of a disease known as "scours" or diarrhea. Calf scours causes more financial loss to herdsmen than any other disease-related problem they encounter. Because the problem of scours is so prevalent, many attempts have been made to formulate a feed supplement that minimizes the incidence of scours. These previous efforts include, among others, the addition of pre-gelatinized starch, optimizing the ratio of casein to whey proteins, forming soluble gels of dairy by-products, and using treated legumes to form protein and starch digestion products from which a feed may be manufactured.

Conventional milk-based replacers suffer from a number of drawbacks. However one such drawback relates to the high cost of milk source ingredients. This cost issue presents the conundrum that, while milk replacer compositions are designed to obviate the need for milk in those cases when the mother's milk is commercially important, the milk replacer composition still must use some amount of milk products in order to keep a young animal healthy.

Often, these above problems are addressed through the development of variety of milk replacer compositions. Indian Patent Application No. 1278/MUM/2006 discloses a milk Replacer formulation for calves comprising of a mixture of cereals and their by-products, oil seed extraction residues, milk substitute, sources of fat, palatability enhancers, mineral nutrients, antibiotics, vitamins, growth promoters and preservatives. One calf milk replacer described in U.S. Pat. No. 5,128,167 include, as ingredients, dried milk, dried whey, dried whey protein concentrate, dextrose, and various vitamins and minerals. U.S. Pat. No. 4,614,653 discloses an improved flowable milk replacer concentrate having good shelf stability and ready reconstitutability is provided for the feeding of monograstic animals, this concentrate can be readily reconstituted to provide a milk replacer. U.S. Pat. No. 5,756,132 disclose milk replacers employed in feeding very young calves to increase the rate of weight gain. It has been reported that calves undergo a surprising rate of weight gain when fed a milk replacer that contains both dextrose and brewers yeast. The invention disclosed in WO 0048474 relates to calf milk replacer compositions, containing substantially no skimmed milk powder, and comprise: vegetable protein concentrate or isolate and a carbohydrate source comprising 10-90% processed starch and 90-10% maltodextrin, together with whey powder and/or delactosed whey powder and/or whey protein concentrate, fat and additives. U.S. Pat. No. 6,096,353 disclose a composition useful as a protein source for a milk replacer in animal feed. The composition consists of a combination of hydrolyzed soya proteins and hydrolyzed wheat gluten. The improved milk replacer composition and dry feed compositions for young mammals are disclosed in U.S. Pat. No. 6,541,047 which employ a high quality inedible egg product to minimize or eliminate the need for milk source ingredients or plasma-enhanced food compositions. The U.S. Pat. No. 4,961,934 discloses milk replacer composition comprises a skim milk powder and/or a soybean meal as a main component, and at least 0.5% by weight of a triglyceride of a medium-chain fatty acid having from 6 to 10 carbon atoms and which is effective to prevent or reduce the incidence of scours and the death rate of infant cattle. JP 57-186445 discloses a milk replacer composition for a calf which comprises the skim milk powder as a principal component with calcium gluconate, and nutrient material, e.g. dried whey, fat or oil, saccharide, animal or vegetable raw material, vitamin or mineral. The milk replacer composition disclosed in JP10-084868 highlights the importance of production method of composition in which any separation of fat and oil is not caused and which has excellent stability and good digestibility and absorbability and does not cause diarrhea by spraying a mixture of fat and oil, lecithin and a polyoxyethylene glycerol fatty ester on a powdery raw material consisting of milk components and granulating the resulting material into granules.

The above existing compositions act as milk replacer composition in feeding the young calf but do not help in overall development of the calf to early complete functional maturity. Further they provide only some relief from the scours problem, but do not eliminate it, nor do they work particularly well to put weight on the young calves. However, these prior art products does not provide the necessary growth factors for young calf. As well, once a calf on a prior art diet gets scours, the farmer will have to administer expensive antibiotics and/or feed supplements that may or may not save the calfs life. These prior art compositions therefore leave significant room for improvement of these compositions with natural components as alternatives.

So there is no existence of the milk replacer composition, which contain medicinal herbs and which address both the problems of overall development of calf to early complete functional maturity by nourishment and prevention of infections such as scours. Hence the present inventor aim is to address the above problems without undesired side effects by developing the herbal milk replacer compositions mainly comprising:
 a) medicinal herbs,
 b) protein and fat sources,
 c) chelated minerals and mineral mixture which are used in functional foods, and
 d) vitamins.

The herbal revolution and its implementation to daily nutrient intake or function food/dietary supplements with desired therapeutic efficacy led the world populations great interest in the herbal compositions. This ultimately led to researchers to develop them in functional food and nutraceuticals and finally to develop marketable products. Functional foods are substances that provide health benefits beyond the normal nutritional values and nutrients added, which are not naturally occurring in that food is called as functional fortified food. The plants are the major source among the Indian masses, since most important foods of mankind as these are not only nutritive but are also sometimes indispensable for the maintenance of health.

It would be desirable to more widely employ natural agents such as herbal mixtures in order to benefit from their safe and beneficial activity. In particular, it would be desirable to use natural agents to induce a more rapid response from herbal medicines by stimulating their beneficial action. The desirability of a combination of natural agents would be dependent, however, upon the continued absence of adverse side effects.

To achieve the foregoing and other objects and in accordance with, the purpose of the present invention, as embodied and broadly described herein, the compositions and process of preparation thereof.

OBJECTS OF THE INVENTION

It is a primary object of the present invention to provide novel herbal milk replacer compositions for overall development of calf to early complete functional maturity along with efficient replacement of the cattle milk.

Another object of the invention is to provide herbal milk replacer compositions as aforesaid which are highly effective in preventing any infection to calf such as scours by boosting the immune system.

A further object of the invention is to provide herbal milk replacer compositions as aforesaid, which do not produce any undesirable byproducts, which do not cause any side effects to the calf.

A further object of the invention is to provide herbal milk replacer compositions as aforesaid, which are safe and practical to use with little technical expertise.

It is a further object of the present invention to provide herbal milk replacer compositions having a long shelf life.

A further object of the invention is to provide herbal compositions as aforesaid, which are cost effective as compared to the existing conventional milk replacer compositions.

STATEMENT OF THE INVENTION

Herbal milk replacer compositions for calf comprising effective amount of an mixture of herbal extract and/or at least one bioactive fraction from medicinal herbs and one or more additives selected from Energy Source, Protein Source, Chelated/organic Mineral Mixture, Vitamins, Salt, Toxin destroyer and Biocide. The mixture of herbal extract comprising medicinal herbs selected from *Emblica officinalis, Tinospora cordifolia, Embelia basaal, Cyprus rotundus, Asparagus racemosus* and *Lepidium sativam*. The effective amount of an extract or bioactive fraction ranges 10 to 30% (w/w) *Emblica officinalis*, 15 to 40% (w/w) *Tinospora cordifolia*, 5 to 20% (w/w) *Embelia basaal*, 5 to 25% (w/w) *Cyprus rotundus*, 10 to 30% (w/w) *Asparagus racemosus* and 5 to 20% (w/w) *Lepidium sativam*. The effective amount of an extract or bioactive fraction more preferably 20% (w/w) *Emblica officinalis*, 25% (w/w) *Tinospora cordifolia*, 10% (w/w) *Embelia basaal*, 15% (w/w) *Cyprus rotundus*, 20% (w/w) *Asparagus racemosus*, and 10% (w/w) *Lepidium sativam*. The effective amount is 1 to 10% (w/w) herbal mixture, 30 to 70% (w/w) Energy Source, 20 to 70% (w/w) Protein Source, 2% (w/w) Chelated/organic Mineral Mixture, 1% (w/w) Salt, 0.1% (w/w) Vitamins, 0.1% (w/w) Toxin Destroyer, 0.03% (w/w) Biocide. The effective amount is preferably 3% (w/w) herbal mixture, 47.8% (w/w) Energy Source, 46% (w/w) Protein Source, 2% (w/w) Chelated/organic Mineral Mixture, 1% (w/w) Salt, 0.1% (w/w) Vitamins, 0.1% (w/w) Toxin Destroyer, 0.03% (w/w) Biocide. The Energy Source is 20 to 50% (w/w) maize flour preferably 30% (w/w), 10 to 30% (w/w) wheat flour preferably 16% (w/w), 1 to 2% (w/w) bypass fat preferably 1.5% (w/w) and 0.2 to 0.5% (w/w) ground nut extract preferably 0.3% (w/w). The Protein Source is 10 to 30% (w/w) soya flour preferably 20% (w/w), 5 to 20% (w/w) skim milk powder preferably 10% (w/w) and 10 to 40% (w/w) maize gluten preferably 16%

(w/w). The process for preparation of herbal milk replacer composition for calf comprising:
a) Obtaining the part of medicinal herb from a group comprising leaves, bark, root and aerial parts;
b) drying the plant part of step (a);
c) powdering the dried plant material of step (b) to a coarse powder;
d) mixing the effective amount by weight of powdered or the concentrated extract of medicinal herb to obtain the herbal mixture;
e) the above herbal mixture is added with one or more ingredients selected from Energy Source, Protein Source, Chelated/organic Mineral Mixture, Vitamins, Salt, Toxin destroyer and Biocide to obtain the herbal milk replacer composition.

DETAILED DESCRIPTION OF THE INVENTION

The present invention relates generally to herbal milk replacer compositions for feeding animals, particularly young animals, and its method of making and feeding, and more particularly relates to shelf-stable and cheaper herbal milk replacer compositions for body weight gain along with overall development of calves to early complete functional maturity and also prevents any infection by acting as immunobooster. The herbal milk replacer compositions comprises an effective amount of an extract and/or at least one bioactive fraction from herbs and one or more additives selected from Energy Source, Protein Source, Chelated/organic Mineral Mixture, Vitamins, Salt, Toxin destroyer and Biocide and process for the preparation of such extracts and herbal milk replacer compositions.

By feeding the calf with herbal milk replacer composition along with the concentrate feed, the composition enhances the development of calf internally and successfully reduces the time period required for complete functional maturity. This invention provides a unique approach to make herbal milk replacer compositions that serves the dual purpose as reduces the time period required for complete functional maturity in calf by overall development and also works as preventive measure for infections such as scours by acting as immunobooster in cattle.

The invention is a herbal milk replacer formulation of an effective amount of an mixture of herbal extract and/or at least one bioactive fraction from medicinal herbs; along with one or more additives selected from Energy source, Protein Source, Chelated/organic Mineral. Mixture, Vitamins, Salt, Toxin destroyer and Biocide and process for the preparation of such extracts and herbal milk replacer compositions. The herbal mixture comprising the medicinal herbs such as *Emblica officinalis, Tribulus terrestris, Tinospora cordifolia, Embelia basaal, Cyprus rotundus, Picrorhiza kurroa, Withania somnifera, Asparagus racemosus, Ipomoea digitata, Phyllanthus amarus* and *Lepidium sativam* etc.; The energy source is selected from maize flour, wheat flour, bypass fat and ground nut extract. The protein source is selected from soya flour, skim milk powder, maize gluten. By properly adjusting a particular component in the herbal milk replacer composition which makes the availability of nutrients and nourishes the calf internally and which results the overall development of calf.

The synergistic formulation also acts as a preventive measure for scours in calf by boosting the natural defense mechanism, strengthening the anti-oxidant mechanism and also by maintaining healthy epithelial and keratin lining.

The synergistic action of the medicinal herbs and protein and energy source along with vitamins and chelated/organic minerals makes the calf to develop fastly towards the complete functional maturity and which is a major economic gain for herdsman. Also acts as a preventive medicine for any infections in calf. So it serves a dual purpose.

As discussed above, the raising of calves on a conventional milk replacer is difficult for the herdsman as currently available formulated products are not nutritionally equivalent to the mother's milk, a great deal of labor is necessary to hand feed the calves, and the young calves, frequently fail to thrive on these nutritionally deficient products. In contrast to these problems experienced with prior art milk replacers, herbal milk replacer compositions according to the present invention yield an increased survival rate, an increased rate of growth, and increased overall well being of young calves over that of calves fed on conventional milk replacer diet. In addition, young calves fed the present milk replacer composition transfer more quickly to solid feed, thereby reducing the overall labor required by the caretaker, including food preparation time and hand feeding.

The herbal milk replacer compositions can be used in several forms: powdered feed form, concentrate form, blender form and base mix form.

The compositions of herbal milk replacer mainly comprise the following ingredients in the proportion as mentioned below:

| | | |
|---|---|---|
| 1. | Herbal Mixture | 1-10% (w/w) of total composition; |
| 2. | Energy Source | 30-70% (w/w) of total composition; |
| 3. | Protein Source | 20-70% (w/w) of total composition; |
| 4. | Chelated/organic Mineral Mixture | 2% (w/w) of total composition; |
| 5. | Salt | 1% (w/w) of total composition; |
| 6. | Vitamins | 0.1% (w/w) of total composition; |
| 7. | Toxin Destroyer | 0.1% (w/w) of total composition; |
| 8. | Biocide | 0.03% (w/w) of total composition. |

1. Herbal Mixture:

The medicinal herbs which comprise the core of the herbal milk replacer compositions are selected from the following group:

1.1 *Emblica officinalis*: Family—Euphorbiaceae

The bark of Amla is gray in color and peals in irregular patches. Its feathery leaves, which smell like lemon, are of linear oblong shape and size 10 to 12 mm length and 3 to 6 mm width. Its flowers are monoecioius having greenish yellow color. They grow in auxiliary clusters and start appearing in the beginning of spring season.

1.2 *Tribulus terrestris*: Family—Zygophyllaceae

It is a flowering plant and is native to warm temperate and tropical regions of the Old World in southern Europe, southern Asia, throughout Africa, and in northern Australia. It can thrive even in desert climates and poor soil. Like many weedy species, this plant has many common names. Puncture Vine, Caltrop, Yellow Vine, and Goathead are the most widely used. It is a taprooted herbaceous perennial plant that grows as a summer annual in colder climates. The stems radiate from the crown to a diameter of about 10 cm to over 1 m, often branching. They are usually prostrate, forming flat patches, though they may grow more upwards in shade or among taller plants. The leaves are pinnately compound with leaflets less than a quarter-inch long. The flowers are 4-10 mm wide, with five lemon-yellow petals. A week after each flower blooms, it is followed by a fruit that easily falls apart into four or five single-seeded nutlets. The nutlets or "seeds" are hard and bear two to three sharp spines, 10 mm long and 4-6 mm broad point-to-point. These nutlets strikingly resemble goats' or bulls' heads; the "horns" are sharp enough to puncture bicycle tires and to cause painful injury to bare feet.

1.3 *Tinospora cordifolia*: Family—Meninspermaceae
It is a large, climbing shrub and grows to 1.0 meters (3.3 feet) high by 0.5 meters (1.65 feet) wide and prefers many types of soil ranging from acid to alkaline and partial to full sun with moderate moisture. This plant has hermaphrodite flowers.

1.4 *Embelia basaal* Family—Myrsinaceae
*E. Basaal*, an Indian variety, with larger elliptical leaves, more or less downy, is useful in various ways. The young leaves, in combination with ginger, are used as a gargle for sore throats, the dried bark of the root as a remedy for toothache, and the ground berries, mixed with butter or lard, made into an ointment and laid on the forehead for pleuritis.

1.5 *Cyprus rotundus* (Mustaka) Family—Cyperaceae
Mustaka was held in high esteem by the ancient sage's of India. This super bulb has been used throughout the ages for the treatment of numerous illnesses. It enjoys an important place among medicinal herbs in India since ancient times. Vagbhata has admired it as the drug of choice for any type of fever. He has also mentioned it as dipaniya—an appetizer, pacaniya—digestant and sangrahi—anti-diarrhoeal. Maharishi Charaka has categorized it as trptighna—anti-saturative, trsna nigra—haniya—thirst relieving, lekhaniya—reducing herb, kandughna—anti-pruritic and stany sodhana—lactodepurant herb. It is also well known for its amapacaka—digests ama and svedala—diaphoretic properties. The plant grows all over India up to 2000 meters altitude, especially on the banks of streams and rivers. A perennial herb grows 0.33-1 meter tall, branches long and with three edges. The spiklets in compound umbels are 5-20 cm long. The rhizomes are blackish, hard, fragrant tubers and aerial stems triquetrous. The fruits are small, ovoid and the seeds tiny, numerous.

1.6 *Picrorhiza kurroa* Family—Scrophulariaceae
*Picrorhiza kurroa* also known as kutki is found in the North-Western Himalayan region from Kashmir to Kumaun and Garhwal regions in India and Nepal. It is a small perennial herb from the Scrophulariaceae family. The rhizome of *Picrorhiza* has been traditionally used to treat worms, constipation, low fever, scorpion sting, asthma and ailments affecting the liver. Current research on *Picrorhiza kurroa* has focused on its hepatoprotective, anticholestatic, antioxidant, and immune-modulating activity.

1.7 *Withania somnifera*: Family—Solanaceae
It is an erect, evergreen, grayish tomentose shrub 0.3-2 m tall, with fairly long, stout, fleshy, whitish-brown roots. Leaves simple, alternate or subopposite, broadly ovate, glabrous, 5-12 cm long and 2.5-7 cm wide, apex subacute, base un equal, marginsentire, finely stellate-pubescent beneath; main nerves about 6 pairs; petioles 0.3-1.7 cm long. The roots are considered alternative, germicidal, aphrodisiac and diuretic; they are used in Ayurveda to treat ulcers, fever, dyspnoea, cough, consumption, dropsy, rheumatism, toxicosis and memory loss. The powdered roots mixed with equal parts of honey and ghee is thought to be beneficial for impotence or seminal debility. The roots as well as the bruised leaves, are also used externally to treat ulcers, painful swellings and scabies. The total alkaloids present in the roots produce relaxant and anti spasmodic effects. The fruits and seeds are diuretic. The leaves are considered anthelmintic and bitter, and their infusion is given to relieve fever.

1.8 *Asparagus racemosus*: Family—Liliaceae
It is a tall climbing, much-branched, spiny shrub with annual woody, white—grey or brown stems armed with strong, straight or recurved spines 0.5-1.3 cm long; rootstock short, tuberous, bearing numerous fusiform, succulent tuberous roots 30-100 cm long and 1-2 cm thick. Flowers white, fragrant, small, crowded in simple and branched racemes 5-15 cm long. Fruits globose, red when ripe, 3-lobed, 0.4-0.6 cm in diameter.

1.9 *Pueraria tuberose*: Family—Fabaceae
It is a coarse, high-climbing, twining, trailing and perennial vine. The huge root, which can grow to the size of a human body, is the source of medicinal preparations used in traditional Chinese medicine and modern herbal products. Habitat is dry deciduous to moist deciduous forests.

1.10 *Ipomoea digitata*: Family—Convolvulaceae
The genus occurs throughout the tropical and subtropical regions of the world, and comprises annual and perennial herbaceous plants, lianas, shrubs and small trees; most of the species are twining climbing plants.

1.11 *Lepidium sativum*: Family—Brassicaceae
It is a fast-growing, edible plant botanically related to watercress and mustard and sharing their peppery, tangy flavor and aroma. In some regions, garden cress is known as garden pepper cress, pepper grass or pepperwort. Garden cress is a green perennial plant used as a leaf vegetable consumed by humans typically as a garnish. Undisturbed garden cress can grow to a height of two feet with minimal maintenance. When mature, garden cress produces white flowers, and small seedpods. Garden cress is used as a medicine in India in the system of ayurveda to prevent postnatal complications. Cress may be given to pet birds such as budgerigars for a healthy and fresh treat.

TABLE 1

Details of the medicinal herbs used in herbal milk replacer compositions for calves are as below:

| S. No | Latin Binomial | Common Names | Geographical Distribution | Parts Used | Quantity | Adverse Effects |
|---|---|---|---|---|---|---|
| 1 | *Emblica officinalis* | Amala | Throughout India | Fruit | 10-30% Preferably 20% | None |
| 2 | *Tinospora cordifolia* | Gulvel | Throughout India | Stem | 15-40% Preferably 25% | None |
| 3 | *Embelia basaal* | Vavding | Throughout | Seeds | 5-20% | None |

TABLE 1-continued

Details of the medicinal herbs used in herbal milk replacer compositions for calves are as below:

| S. No | Latin Binomial | Common Names | Geographical Distribution | Parts Used | Quantity | Adverse Effects |
|---|---|---|---|---|---|---|
| | | | India | | Preferably 10% | |
| 4 | Cyprus rotundus | Nagarmotha | Throughout India | Roots | 5-25% Preferably 15% | None |
| 5 | Asparagus racemosus | Shatawari | Throughout India | Roots or Leaves | 10-30% Preferably 20% | None |
| 6 | Lepidium sativam | Vardhara | Throughout India | Seeds | 5-20% Preferably 10% | None |
| 7 | Tribulus terrestris | Gokhru | Throughout India | Fruit | 10-30% Preferably 10% | None |
| 8 | Picrorhiza kurroa | Kutki | North-Western Himalayan region, India and Nepal | Roots | 10-25% Preferably 15% | None |
| 9 | Withania somnifera | Ashwagandha | Throughout India | Roots or Leaves | 20-40% Preferably 25% | None |
| 10 | Pueraria tuberosa | Bhuikovala | Throughout India | Roots | 10-25% Preferably 15% | None |
| 11 | Ipomoea digitata | Vidarikand | Throughout India | Roots | 5-20% Preferably 10% | None |

2. Energy Source:

The energy source is selected from maize flour, wheat flour, bypass fat and ground nut extract. The energy source is added in the range of 20-50% (w/w) maize flour preferably 30% (w/w), 10-30% (w/w) wheat flour preferably 16% (w/w), 1-2% (w/w) bypass fat preferably 1.5% (w/w) and 0.2-0.5% (w/w) ground nut extract preferably 0.3% (w/w).

3. Protein Source:

The protein source is selected from soya flour, skim milk powder, maize gluten. The protein source is added in the range of 10-30% (w/w) soya flour preferably 20% (w/w), 5-20% (w/w) skim milk powder preferably 10% (w/w) and 10-40% (w/w) maize gluten preferably 16% (w/w).

4. Chelated/Organic Mineral Mixture:

The chelated/organic mineral mixture which mainly consists of the following:

| Chelated Mineral | % by weight |
|---|---|
| Zinc | 5 to 10 |
| Manganese | 1 to 4 |
| Copper | 0.5 to 2 |
| Cobalt | 0.05 to 0.25 |
| Selenium | 0.01 to 0.1 |
| Chromium | 0.05 to 0.2 |
| Iodine | 0.01 to 0.1 |
| Methomin | 5 to 60 |
| Tricalcium phosphate | 30 to 35 |

Preparation of Chelated/Organic Mineral Mixture:

The chelated/organic minerals preferably menthomins chelated are prepared by mixing 8% (w/w) zinc, 2% (w/w) manganese, 1.2% (w/w) copper, 0.12% (w/w) cobalt, 0.05% (w/w) selenium, 0.09% (w/w) chromium, 0.04% (w/w) iodine, methomin and tricalcium phosphate. The chelated mineral mixture is added to the herbal composition in a proportion of 2% (w/w) of total composition.

5. Salt:

The salt used to prepare the composition is sodium chloride and which is added in a proportion of 1% (w/w) of total composition.

6. Vitamins:

Mixture # 1: The vitamins are mixed in the following proportion-

| Vitamin | Nutritional value per gram |
|---|---|
| Vitamin A | 80,000-85,000 IU |
| Vitamin $D_3$ | 10,000-15,000 IU |
| Vitamin K | 8-12 mg |
| Vitamin $B_2$ | 40-60 mg |
| Vitamin $B_{12}$ | 12-18 mcg |

Mixture # 2: The vitamins are mixed in the following proportion-

| Vitamin | Nutritional value per gram |
|---|---|
| Vitamin $B_1$ | 7-9 mg |
| Vitamin $B_2$ | 3-5 mg |
| Vitamin $B_6$ | 14-18 mg |
| Vitamin $B_{12}$ | 70-90 mcg |
| Niacin | 110-130 mg |
| Folic Acid | 3.0-4.0 mg |
| Vitamin E | 75-85 mg |

The vitamin mixture #1 or #2 may be added to the herbal composition in a proportion of 0.1% (w/w) of total composition.

7. Toxin Destroyer:

The toxin destroyer used in the composition is BioFix in a proportion of 0.1% (w/w) of total composition.

8. Biocide:

The biocide used in the composition is Hygisoft Spray in a proportion of 0.03% (w/w) of total composition.

The composition of an effective amount of mixture of herbs and one or more additives selected from Energy Source, Protein Source, Chelated/organic Mineral Mixture, Vitamins, Salt, Toxin destroyer and Biocide to obtain the herbal milk replacer composition for calf; balanced to deliver necessary functions at a particular point in the cattle's digestive system. The herbal mixture contains an extract and/or at least one bioactive fraction from medicinal, herbs such as *Emblica officinalis, Tinospora cordifolia, Embelia basaal, Cyprus rotundus, Asparagus racemosus*, and *Lepidium sativam*. The energy source is selected from maize flour, wheat flour, bypass fat and ground nut extract. The protein source is selected from soya flour, skim milk powder, maize gluten. By properly adjusting a particular component in the composition to make bioavailability of essential nutrients in the intestine of calf for absorption, which enhances the overall health of calf. The synergistic formulation replaces the cattle milk and maintains overall growth of the calf by increasing the weight gain by calve and also helpful in achieving the early conception. The compositions can be used in several forms: powdered feed form, concentrate form, blender form and base mix form.

Process for Preparation of Herbal Milk Replacer Composition:

Method-I

The present invention herbal milk replacer compositions are prepared by one type of method comprising the following steps:

a) Obtaining the part of medicinal herb from a group comprising leaves, bark, root and aerial parts;
b) drying the plant part of step (a);
c) powdering the dried plant material of step (b) to a coarse powder;
d) extracting the powdered dried plant material at a temperature in the range of 30 to 85° C.;
e) extracting the plant material with water or alcohol or mixture of both for a period ranges from 6 hours to 6 days;
f) concentrating the obtained extract under reduced pressure at a temperature in the range of 40 to 85° C.;
g) the concentrated extract is subjected to removal of solvent;
h) mixing the effective amount by weight of above concentrated extract of medicinal herb selected from the group of *Emblica officinalis, Tinospora cordifolia, Embelia basaal, Cyprus rotundus, Asparagus racemosus* and *Lepidium sativam*. to obtain the herbal mixture;
i) the above herbal mixture is added with one or more of the ingredients selected from Energy Source such as maize flour, wheat flour, bypass fat and ground nut extract; Protein Source such as soya flour, skim milk powder, maize gluten; Chelated/organic Mineral Mixture, Vitamins, Salt, Toxin destroyer and Biocide to obtain the herbal milk replacer composition for calf.

Method-II

The present invention herbal milk replacer compositions are prepared by another type of method comprising the steps as below:

a) Obtaining the part of medicinal herb from a group comprising leaves, bark, root and aerial parts;
b) drying the plant part of step (a);
c) powdering the dried plant material of step (b) to a coarse powder;
d) the dried and powdered plant material obtained in step (c) can be used directly to prepare the feed compositions by mixing the effective amount by weight of medicinal herb selected from the group of *Emblica officinalis, Tinospora cordifolia, Embelia basaal, Cyprus rotundus, Asparagus racemosus* and *Lepidium sativam* to obtain the herbal mixture;
e) the above herbal mixture is added with one or more of the ingredients selected from Energy Source such as maize flour, wheat flour, bypass fat and ground nut extract; Protein Source such as soya flour, skim milk powder, maize gluten; Chelated/organic Mineral Mixture, Vitamins, Salt, Toxin destroyer and Biocide to obtain the herbal milk replacer composition for calf.

EXAMPLES

The following specific examples presented to illustrate the herbal milk replacer compositions for calf which are prepared by above said method I or II but do not limit the scope of the invention and additional compositions are being prepared and tested.

TABLE 2

Specific herbal mixtures prepared are as following:

| | % by weight | | | | |
|---|---|---|---|---|---|
| Medicinal Herb | I | II | III | IV | V |
| *Emblica officinalis* | 20 | 25 | 15 | 10 | 25 |
| *Tinospora cordifolia* | 25 | 20 | 25 | 25 | 20 |
| *Embelia basaal* | 10 | 15 | 15 | 15 | 15 |
| *Cyprus rotundus* | 15 | 10 | 10 | 15 | 15 |
| *Asparagus racemosus* | 20 | 15 | 15 | 15 | 10 |
| *Lepidium sativam* | 10 | 15 | 20 | 20 | 15 |

TABLE 3

Specific herbal Compositions prepared are as following:

| | Composition (% by weight) | | | | |
|---|---|---|---|---|---|
| Ingredient | I | II | III | IV | V |
| Herbal Mixture | 3 | 2 | 5 | 7 | 9 |
| Energy Source | 47.8 | 45 | 50 | 60 | 35 |
| Protein Source | 46 | 49.5 | 41.5 | 30.5 | 54 |
| Chelated/organic Mineral Mixture | 2 | 2 | 2 | 2 | 2 |
| Salt | 1 | 1 | 1 | 1 | — |
| Vitamins | 0.1 | 0.1 | 0.1 | 0.1 | — |
| Toxin Destroyer | 0.1 | 0.1 | 0.1 | 0.1 | — |
| Biocide | 0.03 | 0.03 | 0.03 | 0.03 | — |

The trials were carried out on 60 Cross-breed/indigenous cow calves of different age groups and which are divided into two groups of Control group and Treatment group. The control group cows were fed with conventional milk replacer. The Treatment group cows were fed for 90 days with herbal milk replacer composition (I) in a dose of 60 g/day and after 90$^{th}$ day the cow calf (Treatment group) were fed till 365 days with herbal milk replacer composition (I) in a dose of 120 g/day. During the course of feeding, the body weight gain of the calf is measured after every week and it is found that the treatment group cow calf have gained average body weight of 150-200 g/day in comparison to control group as given in Table. 4.

TABLE 4

The average body weight gain per day (gms) of Control and Treatment group in Cow Calf.

| S. No. | Age group (Months) | No. of Animals | | Average Body Weight gain per day (gms) | |
| --- | --- | --- | --- | --- | --- |
| | | Control Group | Treatment group | Control Group | Treatment group |
| 1 | 0-3 | 10 | 10 | 450-500 | 600-700 |
| 2 | 4-6 | 10 | 10 | 550-650 | 600-800 |
| 3 | 7-12 | 10 | 10 | 450-550 | 550-750 |

The invention claimed is:

1. A process for preparation of herbal milk replacer compositions for calf comprising:
   a. obtaining a part of medicinal herb from a group comprising leaves, bark, root and aerial parts;
   b. drying the plant part of step (a);
   c. powdering the dried plant material of step (b) to a coarse powder;
   d. mixing the effective amount by weight of the powdered or the concentrated extract of medicinal herb to obtain an herbal mixture; and,
   e. adding to the above herbal mixture one or more ingredients selected from Energy Source, Protein Source, Chelated/organic Mineral Mixture, Vitamins, Salt, Toxin destroyer and Biocide to obtain the herbal milk replacer composition.

2. An herbal milk replacer composition for calf comprising (i) herbs *Emblica officinalis, Tinospora cordifolia, Embelia basaal, Cyprus rotundus, Asparagus racemosus* and *Lepidium sativam* and/or extracts therefrom and (ii) additives including an energy source, a protein source, a chelated/organic mineral mixture source, a vitamin source, and salt.

3. An herbal milk replacer composition of claim 2 wherein the herbs and/or extracts therefrom are provided in the following ranges: 10 to 30% (w/w) *Emblica officinalis*, 15 to 40% (w/w) *Tinospora cordifolia*, 5 to 20% (w/w) *Embelia basaal*, 5 to 25% (w/w) *Cyprus rotundus*, 10 to 30% (w/w) *Asparagus racemosus* and 5 to 20% (w/w) *Lepidium sativam* wherein the combined percentage does not exceed 100%.

4. An herbal milk replacer composition of claim 2 wherein the energy source is maize flour, wheat flour, bypass fat and/or ground nut extract.

5. An herbal milk replacer composition of claim 2 wherein the protein source is soya flour and/or maize gluten.

6. An herbal milk replacer composition of claim 2 wherein the chelated/organic mineral mixture source includes at least two minerals selected from zinc, manganese, copper, cobalt, selenium, chromium, iodine, methomin and tricalcium phosphate.

7. An herbal milk replacer composition of claim 2 wherein the vitamin source includes at least one vitamin selected from vitamin A, vitamin B1, vitamin B2, vitamin B6, vitamin B12, niacin, folic acid, vitamin D3, vitamin E and vitamin K.

8. An herbal milk replacer composition of claim 2 further comprising a toxin destroyer and a biocide.

9. An herbal milk replacer composition comprising herbs *Asparagus racemosus, Emblica officinalis, Tinospora cordifolia, Embelia basaal* and *Cyprus rotundus* and/or extracts therefrom, and a protein source.

10. An herbal milk replacer composition according to claim 9 further comprising *Lepidium sativam* and/or extracts therefrom.

11. An herbal milk replacer composition according to claim 9 further comprising an energy source, a chelated/organic mineral mixture source, and a vitamin source.

12. An herbal milk replacer composition according to claim 11 further comprising salt.

13. An herbal milk replacer composition according to claim 12 further comprising a toxin destroyer and a biocide.

14. An herbal milk replacer composition according to claim 9 further comprising *Lepidium sativam* and/or extracts therefrom, an energy source, a chelated/organic mineral mixture source, a vitamin source, a toxin destroyer, a biocide and salt.

15. An herbal milk replacer composition according to claim 14 comprising 1 to 10% (w/w) herbs, 30 to 70% (w/w) energy source, 20 to 70% (w/w) protein source, 2% (w/w) chelated/organic mineral mixture, 1% (w/w) salt, 0.1% (w/w) vitamin source, 0.1% (w/w) toxin destroyer and 0.03% (w/w) biocide wherein the combined percentage does not exceed 100%.

16. An herbal milk replacer composition according to claim 15 comprising 2 to 5% (w/w) herbs, 45 to 50% (w/w) energy source, 41.5 to 49.5% (w/w) protein source, 2% (w/w) chelated/organic mineral mixture, 1% (w/w) salt, 0.1% (w/w) vitamin source, 0.1% (w/w) toxin destroyer and 0.03% (w/w) biocide wherein the combined percentage does not exceed 100%.

17. An herbal milk replacer composition according to claim 16 wherein the energy source comprises 20 to 50% (w/w) maize flour, 10 to 30% (w/w) wheat flour, 1 to 2% (w/w) bypass fat and 0.2 to 0.5% (w/w) ground nut extract wherein the combined percentage does not exceed 50%.

18. An herbal milk replacer composition according to claim 16 wherein the protein source comprises 10 to 30% (w/w) soya flour, 5 to 20% (w/w) skim milk powder and 10 to 40% (w/w) maize gluten wherein the total percentage does not exceed 49.5%.

19. An herbal milk replacer composition for calf consisting of (i) herbs consisting of *Emblica officinalis, Tinospora cordifolia, Embelia basaal, Cyprus rotundus, Asparagus racemosus* and *Lepidium sativam* and/or extracts therefrom and (ii) additives consisting of an energy source, a protein source, a chelated/organic mineral mixture source, a vitamin source, salt, a toxin destroyer and a biocide.

20. An herbal milk replacer composition of claim 19 consisting of 2 to 5% (w/w) herbs, 45 to 50% (w/w) energy source, 41.5 to 49.5% (w/w) protein source, 2% (w/w) chelated/organic mineral mixture, 1% (w/w) salt, 0.1% (w/w) vitamin source, 0.1% (w/w) toxin destroyer and 0.03% (w/w) biocide wherein the combined percentage does not exceed 100%.

* * * * *